United States Patent
Rataj

(10) Patent No.: US 11,696,968 B2
(45) Date of Patent: Jul. 11, 2023

(54) CLEAN ROOM AUTOCLAVE BAG AND HOPPER COVER SYSTEM

(71) Applicant: ARAMARK UNIFORM & CAREER APPAREL GROUP, INC., Burbank, CA (US)

(72) Inventor: Michael J. Rataj, Carol Stream, IL (US)

(*) Notice: Subject to any disclaimer, the term of this patent is extended or adjusted under 35 U.S.C. 154(b) by 47 days.

(21) Appl. No.: 17/152,607

(22) Filed: Jan. 19, 2021

(65) Prior Publication Data

US 2021/0138100 A1    May 13, 2021

Related U.S. Application Data

(60) Continuation of application No. 16/213,062, filed on Dec. 7, 2018, now Pat. No. 10,925,990, which is a division of application No. 15/274,332, filed on Sep. 23, 2016, now Pat. No. 10,183,090.

(51) Int. Cl.
*A61L 2/26* (2006.01)
*A61L 2/07* (2006.01)

(52) U.S. Cl.
CPC .......... *A61L 2/26* (2013.01); *A61L 2/07* (2013.01); *A61L 2202/181* (2013.01)

(58) Field of Classification Search
CPC ...... A61L 2/026; A61L 2/07; A61L 2202/181; A47G 27/0206; F24F 1/25; B41J 29/13; D06F 95/002; D06F 95/004; D06F 95/006

USPC ...... 150/154–168; 2/204; 220/287; 422/568, 422/570; 383/61.3, 97

See application file for complete search history.

(56) References Cited

U.S. PATENT DOCUMENTS

| | | | | |
|---|---|---|---|---|
| 2,602,482 | A * | 7/1952 | Lyon | D06F 95/006 383/117 |
| 3,036,616 | A * | 5/1962 | Allen | D06F 95/006 383/38 |
| 5,320,429 | A * | 6/1994 | Toyosawa | D06F 95/008 383/117 |
| 5,746,514 | A * | 5/1998 | Orensten | D06F 95/006 383/88 |
| 5,817,379 | A * | 10/1998 | Rich | D06F 95/006 383/4 |
| 2005/0196075 | A1 * | 9/2005 | Heidel | D06F 95/006 383/117 |
| 2014/0248004 | A1 * | 9/2014 | Weinberg | A45C 7/0077 383/6 |
| 2019/0292719 | A1 * | 9/2019 | Weng | A46B 15/0055 |
| 2021/0222356 | A1 * | 7/2021 | Robinson | D06F 35/005 |

FOREIGN PATENT DOCUMENTS

JP          3206795 U    * 10/2016

* cited by examiner

*Primary Examiner* — Chun Hoi Cheung
(74) *Attorney, Agent, or Firm* — Benjamin Diederich

(57) ABSTRACT

A cleanroom autoclave system including a reusable autoclave breather bag and a reusable fill line hopper cover. The autoclave bag is formed from a launderable abrasion resistant inner fabric layer and a launderable polyester outer fabric layer, and has a zipper closure. The hopper cover is formed from a circular bonnet and an open tubular skirt formed from a launderable polyester fabric, and includes an elastic portion and snaps to secure the hopper cover.

9 Claims, 2 Drawing Sheets

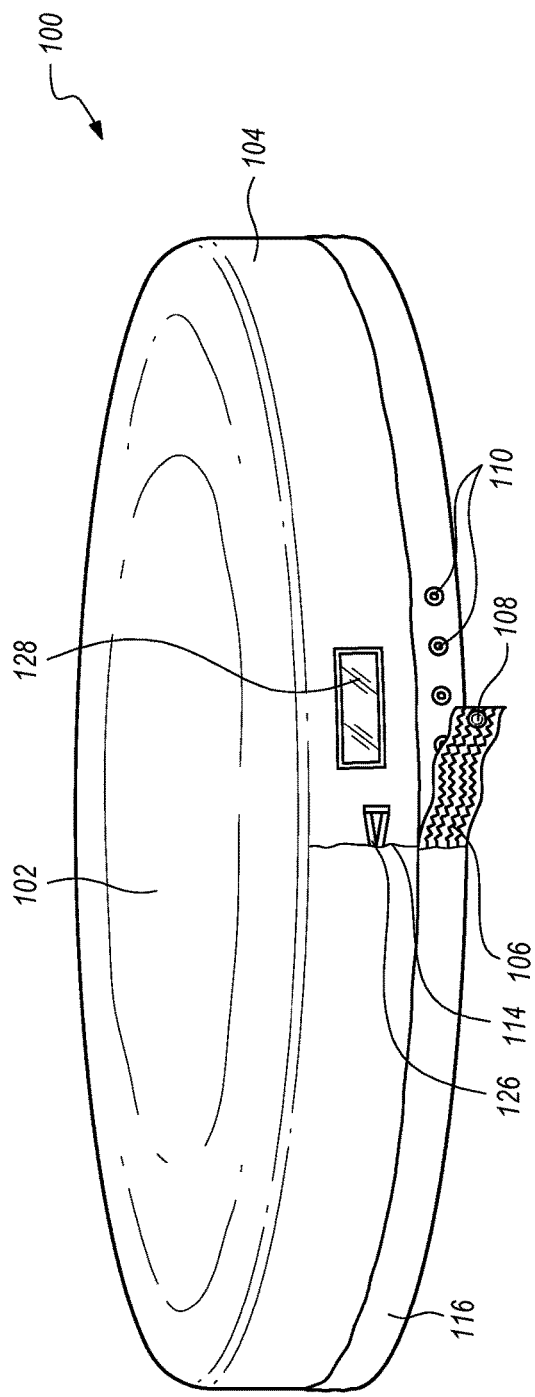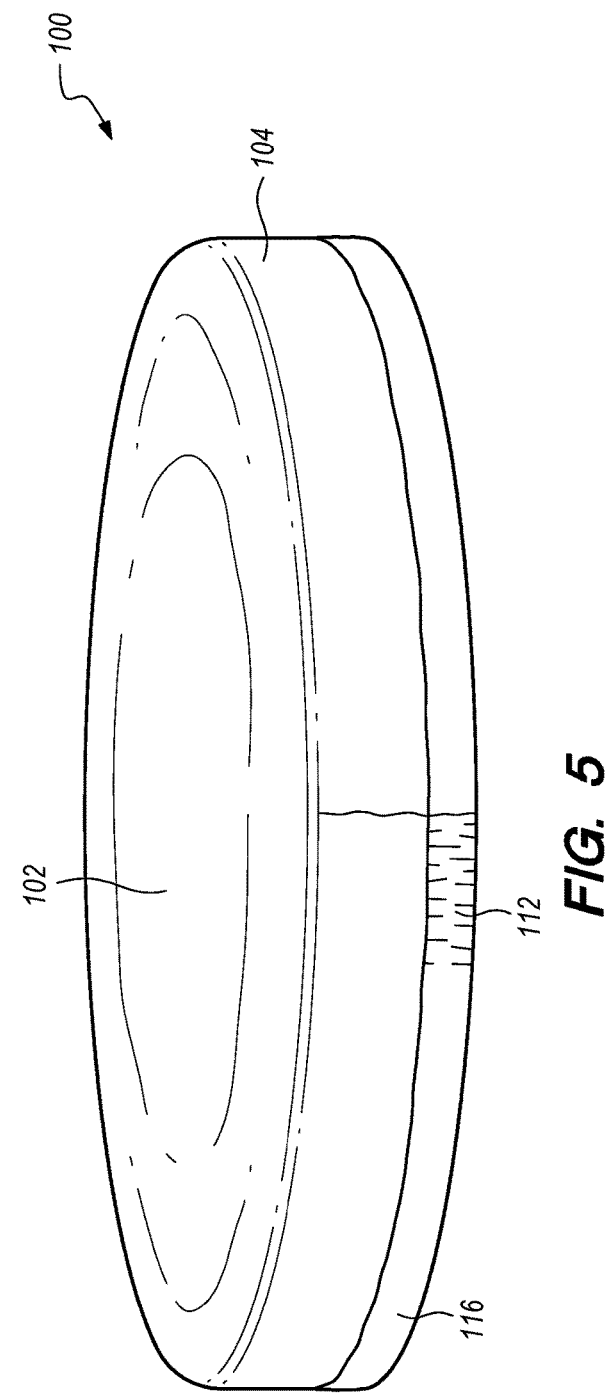

CLEAN ROOM AUTOCLAVE BAG AND HOPPER COVER SYSTEM

CROSS-REFERENCE TO RELATED APPLICATIONS

This application is a continuation of U.S. patent application Ser. No. 16/213,062, filed on Dec. 7, 2018, which is a divisional of U.S. patent application Ser. No. 15/274,332, filed on Sep. 23, 2016, now issued as U.S. Pat. No. 10,183,090, the teachings of all of which are expressly incorporated by reference.

STATEMENT RE: FEDERALLY SPONSORED RESEARCH/DEVELOPMENT

Not Applicable

BACKGROUND

1. Field of the Invention

The present disclosure relates generally to systems and components for sterilizing items within a cleanroom setting, and more particularly to reusable, durable cleanroom autoclave bags and fill equipment hopper covers.

2. Description of the Prior Art

Within a cleanroom setting, for example, in the preparation of pharmaceuticals, food products, or other biologically sensitive products, it is oftentimes necessary to sterilize equipment used within the manufacture of the goods. This is typically accomplished by inserting the equipment to be sterilized into an autoclave bag, and then inserting the bag into an autoclave to be sterilized. The equipment is then preserved in the autoclave bag until its use is needed. Furthermore, in product fill lines, it is often necessary to maintain the sterility of hoppers having an upper opening. The hopper opening is typically covered by some form of sterilized hopper cover.

In general, autoclave bags are typically single-use products made from polyethylene, paper, TYVEK® olefin material produced by E. I. du Pont de Nemours and Company of Wilmington, Del., or combinations thereof. The fact that these products are only used one time is wasteful and environmentally unsound. Furthermore, oftentimes, the equipment to be placed in autoclave bags develop burrs from repeated autoclave cycles, or have sharp edges by design. The burrs or edges can often break through the seal of the polyethylene bag or cause the TYVEK® to particulate. Additionally, non-stock sized breather bags can be expensive to procure and have long lead times to produce, as they are typically only mass produced. Furthermore, prior autoclave bags utilize draw strings or heat seals as closures, which can break in use, or otherwise be difficult to use or open properly. Another issue with certain types of prior autoclave bags are that they are oftentimes produced from plastic materials, such as polypropylene that will outgas as they are heated to the extreme temperatures and pressures needed to achieve sterility. This outgassing, which may be acceptable for use in a dental or surgical setting, may prove to be disastrous in a food or pharmaceutical setting wherein the final product produced on the equipment is consumed by humans.

As such, there is a need for an autoclave bag that is puncture resistant, and will not rip or tear when a sharp piece of equipment is placed within it. Furthermore, there is a need for an autoclave bag that is easy to use, both in inserting and removing equipment from the bag, and in opening and closing the bag. Additionally, there is a need for an autoclave bag that is reusable, to reduce both the economic cost of use and environmental damage that goes along with disposable products and does not produce harmful outgassing when used. Furthermore, there is a need for the autoclave bags that can be produced in various sizes quickly and economically.

BRIEF SUMMARY

In accordance with one embodiment of the present disclosure, there is contemplated a reusable autoclave breather bag for use within a cleanroom setting. The autoclave bag is made up of a pouch formed from a planar first side and a planar second side. The two sides are connected to each other on three edges thereby forming an opening into the pouch at the fourth side. The first side and second side are connected with silicone-free thread. The autoclave bag further includes a zipper attached to the opening along the entire length of the first side and a portion of the second side. In particular, the zipper may extend approximately 1.5 inches on to the second side.

The zipper is also attached to the opening with silicone-free thread. The bag further includes a top portion attached to the zipper with silicone-free thread. The pouch and top portion are made up of a launderable abrasion resistant inner fabric layer and a launderable polyester outer fabric layer.

In particular, the inner fabric layer may be formed from a mid-weight, high-strength polyester fabric having a conductive grid. Furthermore, the inner fabric layer may be formed from a fabric that does not outgas at standard autoclave temperatures and pressures.

The outer fabric layer may be formed from a polyester and carbon fiber blend fabric. In one embodiment, the outer layer fabric is made from an approximately 99 percent polyester and approximately 1 percent carbon fiber fabric.

The bag may further include an identification means, such as a loop attached to the bag and configured to accept a tracking component or a tracking window configured to retain tracking information. The tracking component may be an identification tag.

The present disclosure also envisions a reusable fill line hopper cover for use in a cleanroom setting. The hopper cover is made up of a circular bonnet and an open tubular skirt, both formed from a launderable polyester fabric. The skirt is attached to the bonnet with silicone-free thread, such that it extends downward from the bonnet. The skirt has a hem portion opposite from the bonnet that includes an elastic portion.

The skirt further includes a tab attached to the skirt with silicone-free thread. The tab has at least one snap attached to it, and the skirt further has a plurality of snaps attached directly to the skirt. The plurality of snaps on the skirt are complementary to the at least one snap disposed on the tab. In a preferred embodiment, the tab may feature two female snaps, and the skirt may have four male snaps attached directly to it. The snaps may be formed from stainless steel.

The hopper cover may further include an identification means, such as a loop attached to the hopper cover and configured to accept a tracking component or a tracking window configured to retain tracking information.

The launderable polyester fabric of the hopper cover may be made from a polyester and carbon fiber blend. In a particular embodiment, the fiber blend is approximately 99 percent polyester and approximately 1 percent carbon fiber.

Additionally, the bonnet and skirt may be formed from two layers of the launderable polyester fabric.

Additionally, the present disclosure envisions a cleanroom autoclave system made up of the reusable autoclave breather bag and reusable fill line hopper cover described herein.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 4 is a perspective view of the front side of a hopper cover of the present disclosure; and FIG. 5 is a perspective view of the rear side of the hopper cover shown in FIG. 4.

DETAILED DESCRIPTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Figure 3:
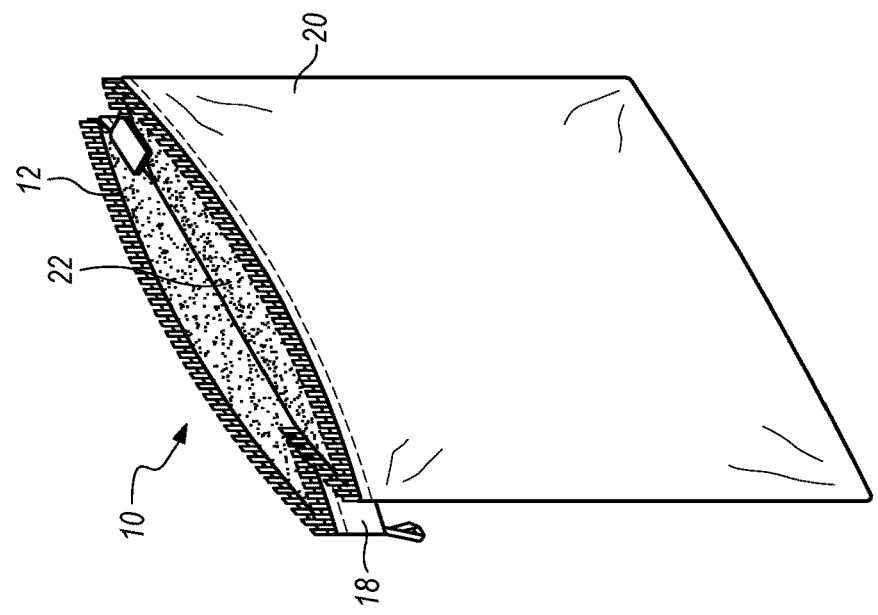
FIG. 3 is a perspective view of the autoclave breather bag shown in FIG. 1 with the zipper open.
Figure 2:
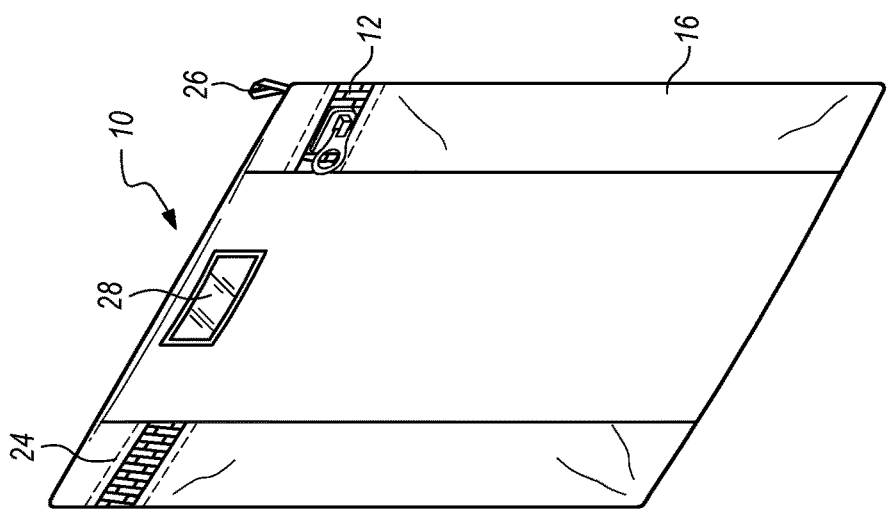
FIG. 2 is a perspective view of the rear side of the autoclave breather bag shown in FIG. 1.
Figure 1:
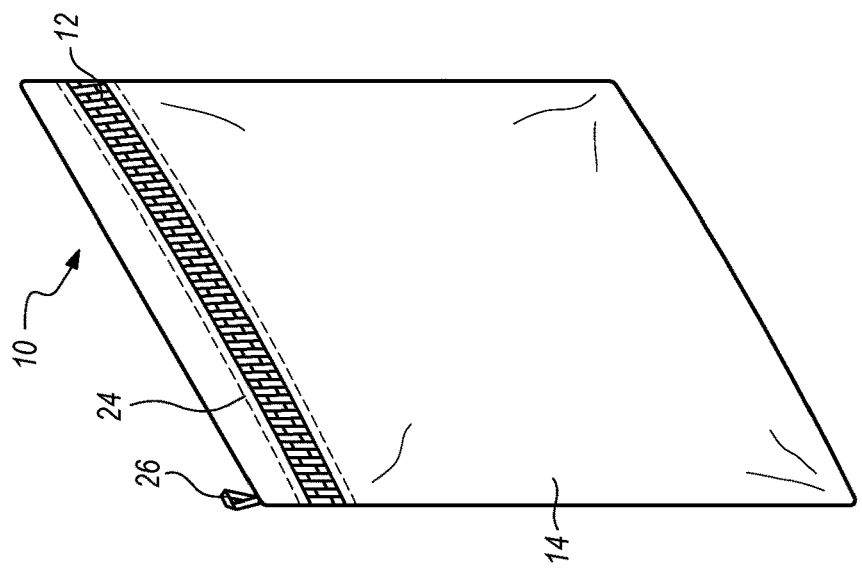
FIG. 1 is a perspective view of the front side of an autoclave breather bag of the present disclosure.

As shown in FIGS. 1-3, one aspect of the present disclosure is a reusable autoclave breather bag 10. The autoclave bag 10 may be utilized in numerous sterilization situations; however, it is preferably used within a cleanroom setting, and more preferably used for autoclaving fill line equipment.

The autoclave bag 10 has a zipper 12 disposed at one end of the bag 10. The zipper 12 preferably wraps completely around a first side 14 of the bag 10 (as shown in FIG. 1) and on to at least a portion of a second side 16 of the bag 10 (as shown in FIG. 2). By wrapping around on to the second side 16, the zipper 12 is able to allow a top portion 18 of the bag 10 located above the zipper 12 to fully open (as shown in FIG. 3), thereby aiding in the insertion and removal of equipment to be sterilized (not shown). In a preferred embodiment, the zipper 12 extends approximately 1.5 inches on to the second side 16 of the bag 10. By using a zipper 12 as the closure for the bag 10, it greatly aids in the usability of the bag by allowing for easy opening and closing, as well as easy insertion of equipment in to the bag. While the zipper 12 will not allow for a hermetic seal of the bag 10, such a seal is unnecessary for its use as the bag 10 is intended to be used within a cleanroom setting, for example with pass-through autoclaves, wherein new foreign material will not be introduced to the equipment contained within.

Furthermore, the autoclave bag 10 comprises a first, outer layer 20 made from a first fabric and a second, inner layer 22 made from a different second fabric. Importantly, both layers 20, 22 are made from launderable materials to allow the autoclave bag 10 to be reused. Additionally, the layers 20, 22 are formed from fibers that will not outgas at standard autoclave temperatures and pressures, and will not release particulate material in use, which can be disastrous in a cleanroom setting.

Importantly, the inner layer 22 is formed from an abrasion resistant fabric to protect the bag 10 from being punctured by the equipment placed within it. Furthermore, the inner layer 22 is made from a fiber having a small pore size to prevent the contamination of the equipment within once autoclaved. In a preferred embodiment, the inner layer 22 is formed from a mid-weight, high strength polyester fabric having a conductive grid. An exemplary material for the inner layer 22 used in a preferred embodiment is CHEM-STAT™ 939T fabric made by Stern & Stern of Hornell, N.Y.

The outer layer 20 is formed from a launderable fiber that will not outgas, but does not need to be as robust as the inner layer 22, as it does not directly come in to contact with the equipment to be sterilized. In a preferred embodiment, the outer layer 20 is formed from a polyester and carbon fiber fabric. In a more preferred embodiment, the outer layer 20 is formed from a fabric comprising approximately 99 percent polyester and approximately 1 percent carbon fiber. An exemplary material for the outer layer 20 used in a preferred embodiment is the MAXIMA® ESD fabric made by Burlington Barrier Products of Greensboro, N.C.

The autoclave bag 10 utilizes a silicone-free thread 24 for all sewn portions of the bag. For example, the zipper 12 is sewn into the bag 10 utilizing the silicone-free thread. The use of silicone-free thread is important to eliminate the particulate risk of using the bag 10 in a cleanroom setting. Additionally, in one embodiment, all edges of the bag 10 are pre-serged with the silicone-free thread 24 to add further overall strength to the bag 10.

By using the above-described materials in forming the autoclave bag 10, it is possible to launder and re-use the bag 10 up to one hundred times before having to dispose of the bag. Reusing the bag 10 this many times leads to a significant decrease in environmental waste, as well as a large economical savings to the user, by not having to replace the autoclave bag after every single use.

The autoclave bag 10 may further comprise at least one identification means. The identification means may be used to track various aspects of the bag's use, including, among other things, the number of times the bag has been used, the date the bag was created and/or first used, the equipment contained within the bag 10, and the like. One example of an identification means is a loop 26 attached to the bag 10. The loop 26 may be utilized to secure an identification tag (not shown) or other tracking component. In one example, the loop 26 is formed from an approximately quarter inch wide piece of grosgrain material, and is positioned at a corner of the bag 10. Another identification means that can alternatively, or additionally, be used with the loop 26, is a tracking window 28 that can have tracking information written on, embedded in, or contained inside of.

An additional aspect of the present disclosure is the ability to form the autoclave bag 10 in various sizes and shapes depending on the needed use. Examples of standard sizes of the bag 10 can include rectangles of approximately ten inches by fifteen inches, twelve inches by forty inches, fifteen inches by twenty inches, thirty-six inches by thirty-six inches, and thirty-six inches by sixty inches. However, these examples should not be seen as limiting, as the bag 10 can be readily formed in various sizes and shapes, and one beneficial aspect of the present disclosure is that custom sizes can be readily and economically produced as needed due to the relative simplicity of manufacturing the bag 10.

As shown in FIGS. 4 and 5, another aspect of the present disclosure is a reusable cover 100. This cover 100 may be utilized to seal and maintain the sterility of fill line hopper equipment openings. Similar to the autoclave bags that are also a part of the present disclosure, the hopper covers 100 are formed from reusable and launderable fabric. However, since the hopper cover 100 will not be coming in to contact with sharp equipment, it does not require the inclusion of an abrasion resistant inner layer.

Indeed, the hopper cover 100 may be formed from the same polyester and carbon fiber blend fabric as used on the outer layer of the autoclave bag 10. Preferably, the hopper cover is formed from a fabric comprising approximately 99 percent polyester and approximately 1 percent carbon fiber, such as the MAXIMA® ESD fabric. The hopper cover 100 may be formed from a single layer of fabric, or may be formed from two layers of the polyester/carbon fiber blend fabric.

In particular, the hopper cover 100 comprises two primary components formed from the fabric: an upper bonnet 102 and a skirt 104 attached to, and extending downwardly from, an outer edge of the bonnet 102.

The bonnet 102 primarily functions to cover, protect, and exclude matter from entering a hopper opening. While it is primarily envisioned as being a circular shape, the bonnet 102 could be formed in various other configurations, such as in the shape of a square or rectangle.

The skirt 104 extends down from the bonnet 102 and functions to secure the hopper cover 100 to the hopper. The skirt 104 is tubular in shape and is formed from one or two pieces of fabric joined at a seam 114. Additionally, the bottom portion of the skirt 104 may be folded up to form a hem 116. The hem 116 comprises an elastic portion 112 to tighten the skirt 104 in place on the hopper.

Positioned on the skirt 104 is a tab 106 that is attached to the skirt 104 at a first end of the tab 106, and having at least one snap fastener 108 positioned at a second, opposite end of the tab 106. Positioned on the skirt 104, is at least one complementary snap fastener 110, to which the at least one tab snap 108 can be reversibly attached. In a preferred embodiment, the tab 106 is an approximately three inch long by three-quarter inch wide piece of webbing attached at its first end at the seam 114 on the hem 116 of the skirt 104, and having two female snaps 108 at its second end. The two female snaps 108 may be positioned approximately one inch apart from each other on the tab 106. In this embodiment, there are four male snaps 110 positioned in series on the hem 116, with the first snap 110 positioned approximately three inches from the seam 114, and each subsequent snap 110 positioned approximately one inch apart from each other. The snaps 108, 110 are formed from a non-reactive material, and are preferably formed from stainless steel.

Accordingly, the hopper cover 100 is configured to be securely attached to a hopper opening by virtue of its elastic portion 112 that initially tightens to the hopper, and the further use of the complementary snaps 108, 110. When the snaps 108, 110 are engaged, the hopper cover 100 is strongly secured to the hopper opening, and is easily removed by unfastening the snaps 108, 110. This is a vast improvement over prior hopper covers, which only utilize elastic, and thus are less secure, or use a drawstring which requires tying a knot, that can be difficult to use in practice.

Similar to the autoclave bag 10, the hopper cover 100 may further include tracking means such as an identification loop 126 positioned at the seam 114 and/or a tracking window 128 located on the skirt 104 or bonnet 102. Furthermore, all of the edges are pre-serged, and all seams are likewise made with silicone-free thread to avoid particulate contamination.

While the hopper cover 100 can be fabricated in various configurations and sizes, a common skirt 104 size would be approximately six inches long and exemplary bonnet 102 diameters include approximately sixteen inches, approximately twenty-one inches, and approximately thirty inches.

The above description is given by way of example, and not limitation. Given the above disclosure, one skilled in the art could devise variations that are within the scope and spirit of the invention disclosed herein, including various sizes, shapes, and configurations of the autoclave bags and hopper covers described herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A reusable autoclave breather bag for use within a cleanroom setting comprising:
    a pouch formed from a planar first side and a planar second side connected to the first side on three edges thereby forming an opening into the pouch;
    a zipper attached to the opening; and
    a top portion attached to the zipper;
    wherein the pouch and top portion comprise:
        a launderable abrasion resistant inner fabric layer, wherein the inner fabric layer is formed from a mid-weight, high-strength polyester fabric having a conductive grid; and
        a launderable outer fabric layer.

2. The reusable autoclave breather bag of claim 1, wherein the inner fabric layer does not outgas at standard autoclave temperatures and pressures.

3. The reusable autoclave breather bag of claim 1, wherein the zipper extends approximately 1.5 inches on to the second side.

4. The reusable autoclave breather bag of claim 1, further comprising an identification means.

5. The reusable autoclave breather bag of claim 4, wherein the identification means is a loop attached to the bag and configured to accept a tracking component.

6. The reusable autoclave breather bag of claim 5, wherein the tracking component is an identification tag.

7. The reusable autoclave breather bag of claim 4, wherein the identification means is tracking window configured to retain tracking information.

8. A reusable autoclave breather bag for use within a cleanroom setting comprising:
    a pouch formed from a planar first side and a planar second side connected to the first side on three edges thereby forming an opening into the pouch;
    a zipper attached to the opening; and
    a top portion attached to the zipper;
    wherein the pouch and top portion comprise:
        a launderable abrasion resistant inner fabric layer; and
        a launderable outer fabric layer, wherein the outer fabric layer is formed from a polyester and carbon fiber blend fabric.

9. The reusable autoclave breather bag of claim 8, wherein the outer layer fabric comprises approximately 99 percent polyester and approximately 1 percent carbon fiber.

* * * * *